Feb. 15, 1944 J. H. JONES Plant Pat. 615
PHLOX
Filed June 2, 1941
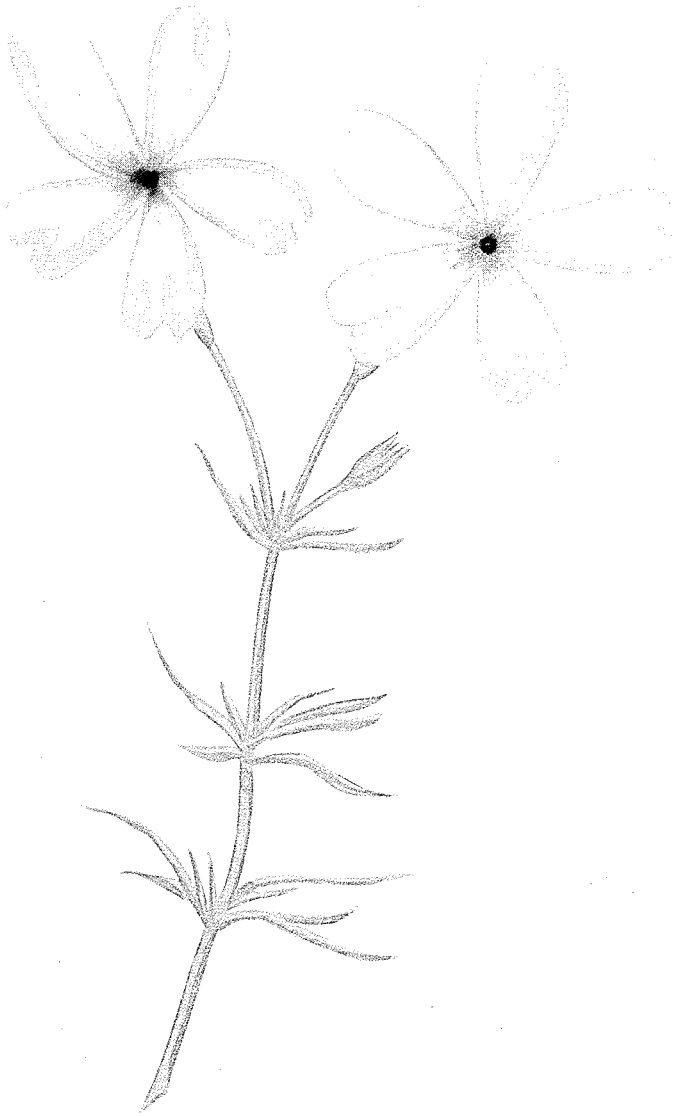
INVENTOR
John Herbert Jones
BY Carmack Waterhouse
ATTORNEY Patented Feb. 15, 1944

Plant Pat. 615

UNITED STATES PATENT OFFICE

615

PHLOX

John Herbert Jones, Cartersville, Ga.

Application June 2, 1941, Serial No. 396,279

1 Claim. (Cl. 47—60)

My invention pertains to a novel and distinct variety of *Phlox nivalis* of a general type similar to *Phlox subulata*.

Both *Phlox subulata* and my phlox are low growing plants with lateral branches radiating from one root stem and resting on the surface of the ground. These lateral branches, when undisturbed for a considerable time, take root and in due course a small plant has developed into a cluster of well rooted plants from approximately 12″ to 24″ across. These lateral branches are substantially surrounded by narrow, hard, prickly leaves, which are closely set on the stem and which radiate from the main stem and which foliage is moss like. Up to this point the nature of *Phlox subulata* and my phlox is substantially similar, with the exception that my phlox has a much more rugged and heavy set foliage, and the branches other than those that lie on the ground grow taller and much stronger than those of the *subulata* type.

From the aforementioned lateral branches, a mass of secondary branches or bloom heads spring upwardly, growing quite erect. These secondary branches also have a rugged growth, each carrying its own weight of bloom as distinguished from the *subulata* type, which is comparatively weak and unable to support itself. The result of this characteristic in my phlox is a blooming plant of large, symmetrical proportions so completely covered with blooms that for several weeks the green foliage can scarcely be seen. My phlox has been found to be highly desirable for beds, borders, rockeries, steep banks and cemeteries.

The plant is very hardy and capable of withstanding subzero temperature, cold weather without damage, being winter hardy in any part of the United States or similar climate without protection and will grow in climates up to at least latitude 55°. It is ready to start blooming as soon as the rigors of winter are over, and is one of the first, if not the first, to bloom in the spring. In a few days the plant is covered with blooms which usually hold on for from six to eight weeks.

The invention is largely a result of steady development or cultivation, starting with and asexually reproducing from a small plant taken from the woods in the hill country of the State of Alabama in about the year 1927. A larger number of plants were reproduced asexually by cuttings and among these new plants was found a new type of phlox having distinctly different characteristics from the other plants. The new plant was set apart from the others and by cultivation and propagating the plant I have been able to uniformly reproduce this phlox by cuttings on a large scale. The drawing is of a single branch of a flower plant being one of the upright stems that grows from the lateral branches, showing the blossoms in full bloom and in their natural colors as nearly as possible to produce artificially. The blossoms are very peculiar and very pleasing as to color, being substantially a deep, rich, vivid pink with an even deeper center. The foliage of my phlox is a very deep green, as distinguished from the light green of the *subulata* type. The individual blossoms are comparatively enormous in a flower of this type with blossoms measuring approximately one and three-eights inches across. The five petals stand apart and have a tendency to quill or curl when a day or so old, which materially enhances the appearance of the bloom.

The en masse effect is one of almost startling brilliance, yet very pleasing to the eye. The plant remains green throughout the year.

The aforementioned plant was transplanted to my garden and each following year the best plants were selected therefrom and reset. Under close attention the plant has been propagated asexually and cultivated to its present state of domestication.

The colors of the petals and center of the flower have been compared with the Rembrandt Color Chart and with Ridgway's "Color Standard and Nomenclature." The nearest color found in Rembrandt's colors for the petals was "Rose Carthame" and the nearest color in Ridgway's "Color Standard and Nomenclature" was found on Plate I, entitled, "Begonia Rose" and for the center in Rembrandt's colors the nearest color found was "Crimson Lake" and in Ridgway's "Color Standard and Nomenclature" the nearest color found was "Carmine" in Plate I.

Now having illustrated and described my new phlox and the method of reproducing the same, what I claim and desire to secure by Letters Patent of the United States is:

A variety of phlox substantially as herein shown and described characterized and distinguished by lateral branches having rugged and deep green foliage of the evergreen character, a mass of upstanding flower bearing stems extending from the lateral branches having at their terminals blossoms having deeper centers, the petals of the blossoms standing apart and having a tendency to curl, such blossoms being in abundance to form a plant of symmetrical proportions substantially covered by the blossoms.

JOHN HERBERT JONES.